US011922621B2

(12) United States Patent
Urman et al.

(10) Patent No.: US 11,922,621 B2
(45) Date of Patent: Mar. 5, 2024

(54) AUTOMATIC FRAME SELECTION FOR 3D MODEL CONSTRUCTION

(71) Applicant: Biosense Webster (Israel) Ltd., Yokneam (IL)

(72) Inventors: Roy Urman, Irvine, CA (US); Liron Shmuel Mizrahi, Kiryat Bialik (IL); Yariv Avraham Amos, Tzorit (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 358 days.

(21) Appl. No.: 17/239,817

(22) Filed: Apr. 26, 2021

(65) Prior Publication Data

US 2022/0343495 A1 Oct. 27, 2022

(51) Int. Cl.
*G06T 7/00* (2017.01)
*G06T 17/00* (2006.01)

(52) U.S. Cl.
CPC ............ *G06T 7/0012* (2013.01); *G06T 17/00* (2013.01); *G06T 2207/20081* (2013.01); *G06T 2207/20084* (2013.01); *G06T 2207/30004* (2013.01)

(58) Field of Classification Search
CPC .................. G06T 7/0012; G06T 17/00; G06T 2207/20081; G06T 2207/20084; G06T 2207/30004; G06T 2207/10132; G06T 2207/10016; G06T 2207/30048; G06T 2207/30168; G06T 7/0002; G06T 2200/04; G06T 2210/41; A61B 5/0044; A61B 5/065; A61B 8/0883; A61B 8/12; A61B 8/4254; A61B 8/469; A61B 8/483; A61B 8/5223; A61B 8/543; A61B 8/5284; A61B 5/318; A61B 8/0891; A61B 8/46; A61B 8/5215; A61B 8/5269; G16H 50/50; G16H 30/20; G16H 50/20
See application file for complete search history.

(56) References Cited

U.S. PATENT DOCUMENTS

| 6,447,450 B1 | 9/2002 | Olstad |
| 8,891,881 B2 | 11/2014 | Gupta et al. |
| 10,143,398 B2 | 12/2018 | Altmann et al. |

(Continued)

FOREIGN PATENT DOCUMENTS

WO    2021222426 A1    11/2021

OTHER PUBLICATIONS

EP Application No. 22169634.7-1126—Extended European Search Report dated Sep. 21, 2022.

(Continued)

*Primary Examiner* — Siamak Harandi
(74) *Attorney, Agent, or Firm* — Notaro, Michalos & Zaccaria P.C.

(57) ABSTRACT

A method includes obtaining, by a processor, a set of ultrasound frames showing a portion of a heart of a subject, identifying a subset of the frames, responsively to the subset having been acquired at one or more predefined phases of at least one physiological cycle of the subject, computing respective image-quality scores for at least the subset of the frames, each of the scores quantifying an image quality with which one or more anatomical portions of interest are shown in a respective one of the frames, and, based on the image-quality scores, selecting, for subsequent use, at least one frame from the subset of the frames. Other embodiments are also described.

20 Claims, 4 Drawing Sheets

(56) References Cited

U.S. PATENT DOCUMENTS

| | | | |
|---|---|---|---|
| 2002/0072670 A1 | 6/2002 | Chenal et al. | |
| 2005/0078791 A1* | 4/2005 | Li | A61B 6/032 378/95 |
| 2006/0253031 A1 | 11/2006 | Altmann et al. | |
| 2011/0152684 A1 | 6/2011 | Altmann et al. | |
| 2016/0217569 A1* | 7/2016 | Bhatia | G16H 30/40 |
| 2017/0360411 A1 | 12/2017 | Rothberg et al. | |
| 2018/0021022 A1 | 1/2018 | Lundberg et al. | |
| 2018/0240551 A1 | 8/2018 | Perrey et al. | |
| 2020/0289094 A1 | 9/2020 | De Jonge et al. | |
| 2021/0145411 A1* | 5/2021 | Aladahalli | A61B 8/4461 |

OTHER PUBLICATIONS

Zayed et al., "Automatic frame selection using CNN in ultrasound elastography," arXiv preprint arXiv:2002.06734 (2020).

Szegedy, Christian, et al., "Going deeper with convolutions," Proceedings of the IEEE conference on computer vision and pattern recognition, 2015.

He, Kaiming, et al., "Deep residual learning for image recognition," Proceedings of the IEEE conference on computer vision and pattern recognition, 2016.

Simonyan, Karen, and Andrew Zisserman, "Very deep convolutional networks for large-scale image recognition," arXiv preprint arXiv:1409.1556 (2014).

Kaur, Taranjit, and Tapan Kumar Gandhi, "Deep convolutional neural networks with transfer learning for automated prain image classification," Machine Vision and Applications 31.3 (2020): 1-16.

Vesal, Sulaiman, et al., "Classification of breast cancer histology images using transfer learning," International conference image analysis and recognition, Springer, Cham, 2018.

European Examination Report for corresponding European Application No. EP 22169634.7 dated Jul. 14, 2023.

* cited by examiner

AUTOMATIC FRAME SELECTION FOR 3D MODEL CONSTRUCTION

FIELD OF THE INVENTION

The present invention is related to the field of medical imaging.

BACKGROUND

U.S. Pat. No. 8,891,881 describes a method for identifying an optimal image frame. The method includes receiving a selection of an anatomical region of interest in an object of interest. Furthermore, the method includes obtaining a plurality of image frames corresponding to the selected anatomical region of interest. The method also includes determining a real-time indicator corresponding to the plurality of acquired image frames, wherein the real-time indicator is representative of quality of an image frame. In addition, the method includes communicating the real-time indicator to aid in selecting an optimal image frame.

U.S. Pat. No. 10,143,398 describes a system and method for imaging a target in a patient's body using a pre-acquired image of the target and a catheter having a position sensor and an ultrasonic imaging sensor. The catheter is placed in the patient's body and positional information of a portion of the catheter in the patient's body is determined using the position sensor. The catheter is used to generate an ultrasonic image of the target using the ultrasonic imaging sensor. An image processor is used for determining positional information for any pixel of the ultrasonic image of the target and registering the pre-acquired image with the ultrasonic image, and a display is used for displaying the registered pre-acquired image and ultrasonic image.

US Patent Application Publication 2017/0360411 describes techniques for guiding an operator to use an ultrasound device. For example, some of the techniques may be used to identify a particular anatomical view of a subject to image with an ultrasound device, guide an operator of the ultrasound device to capture an ultrasound image of the subject that contains the particular anatomical view, and/or analyze the captured ultrasound image to identify medical information about the subject.

US Patent Application Publication 2011/0152684 describes a method for three-dimensional (3D) mapping, including acquiring a plurality of two-dimensional (2D) ultrasonic images of a cavity in a body of a living subject, the 2D images having different respective positions in a 3D reference frame. In each of the 2D ultrasonic images, pixels corresponding to locations within an interior of the cavity are identified. The identified pixels from the plurality of the 2D images are registered in the 3D reference frame so as to define a volume corresponding to the interior of the cavity. An outer surface of the volume is reconstructed, representing an interior surface of the cavity.

Zayed et al., "Automatic frame selection using CNN in ultrasound elastography," arXiv preprint arXiv:2002.06734 (2020), introduces a method using a convolutional neural network (CNN) to determine the suitability of a pair of radiofrequency (RF) frames for elastography, or to automatically choose the best pair of RF frames yielding a high-quality strain image.

SUMMARY OF THE INVENTION

There is provided, in accordance with some embodiments of the present invention, a system including circuitry, configured to receive and process at least one signal tracking at least one physiological cycle of a subject, and a processor. The processor is configured to receive the signal from the circuitry following the processing of the signal. The processor is further configured to obtain a set of ultrasound frames showing a portion of a heart of the subject. The processor is further configured to identify a subset of the frames responsively to the subset having been acquired at one or more predefined phases of the physiological cycle, based on the signal. The processor is further configured to compute respective image-quality scores for at least the subset of the frames, each of the scores quantifying an image quality with which one or more anatomical portions of interest are shown in a respective one of the frames. The processor is further configured to select, for subsequent use, at least one frame from the subset of the frames, based on the image-quality scores.

In some embodiments, the physiological cycle includes a respiratory cycle.

In some embodiments, the physiological cycle includes a cardiac cycle.

In some embodiments, the processor is configured to select the frame for use in building a three-dimensional anatomical model.

In some embodiments, the anatomical portions of interest include an anatomical portion selected from the group of anatomical portions consisting of: a left atrium body, a pulmonary vein (PV), a left atrial appendage, a left ventricle (LV) endocardium, an LV epicardium, a posteromedial papillary muscle, an anterolateral papillary muscle, a left coronary cusp, a right coronary cusp, a non-coronary cusp, and a coronary sinus.

In some embodiments, the processor is configured to compute the image-quality scores using a neural network.

In some embodiments, the set includes between 60 and 120 frames.

In some embodiments, the processor is further configured to:

ascertain that a number of the image-quality scores passing a predefined image-quality-score threshold is less than a predefined frame-number threshold, and in response to the ascertaining, output a warning.

There is further provided, in accordance with some embodiments of the present invention, a method including obtaining, by a processor, a set of ultrasound frames showing a portion of a heart of a subject. The method further includes identifying a subset of the frames, responsively to the subset having been acquired at one or more predefined phases of at least one physiological cycle of the subject. The method further includes computing respective image-quality scores for at least the subset of the frames, each of the scores quantifying an image quality with which one or more anatomical portions of interest are shown in a respective one of the frames. The method further includes, based on the image-quality scores, selecting, for subsequent use, at least one frame from the subset of the frames.

There is further provided, in accordance with some embodiments of the present invention, a computer software product including a tangible non-transitory computer-readable medium in which program instructions are stored. The instructions, when read by a processor, cause the processor to obtain a set of ultrasound frames showing a portion of a heart of a subject. The instructions further cause the processor to identify a subset of the frames, responsively to the subset having been acquired at one or more predefined phases of at least one physiological cycle of the subject. The instructions further cause the processor to compute respective image-quality scores for at least the subset of the frames, each of the scores quantifying an image quality with which one or more anatomical portions of interest are shown in a respective one of the frames. The instructions further cause the processor to select, for subsequent use, at least one frame from the subset of the frames, based on the image-quality scores.

The present invention will be more fully understood from the following detailed description of embodiments thereof, taken together with the drawings, in which:

DETAILED DESCRIPTION OF EMBODIMENTS

Overview

In some applications, information derived from ultrasound frames is incorporated into an anatomical model. However, ultrasound frames may vary greatly from each other with respect to the image quality with which important anatomical features are shown, and it is tedious to manually select those frames having sufficient image quality.

To address this challenge, embodiments of the present invention provide a processor configured to automatically score ultrasound frames for image quality, typically using a trained neural network. Those frames having higher scores are then selected for subsequent use in building the anatomical model, while those frames with lower scores are discarded. Typically, the processor further filters the frames per the cardiac cycle and/or respiratory cycle of the subject from whom the frames were acquired, such that only frames acquired during a particular cardiac phase and/or respiratory phase are selected.

System Description

Figure 1:
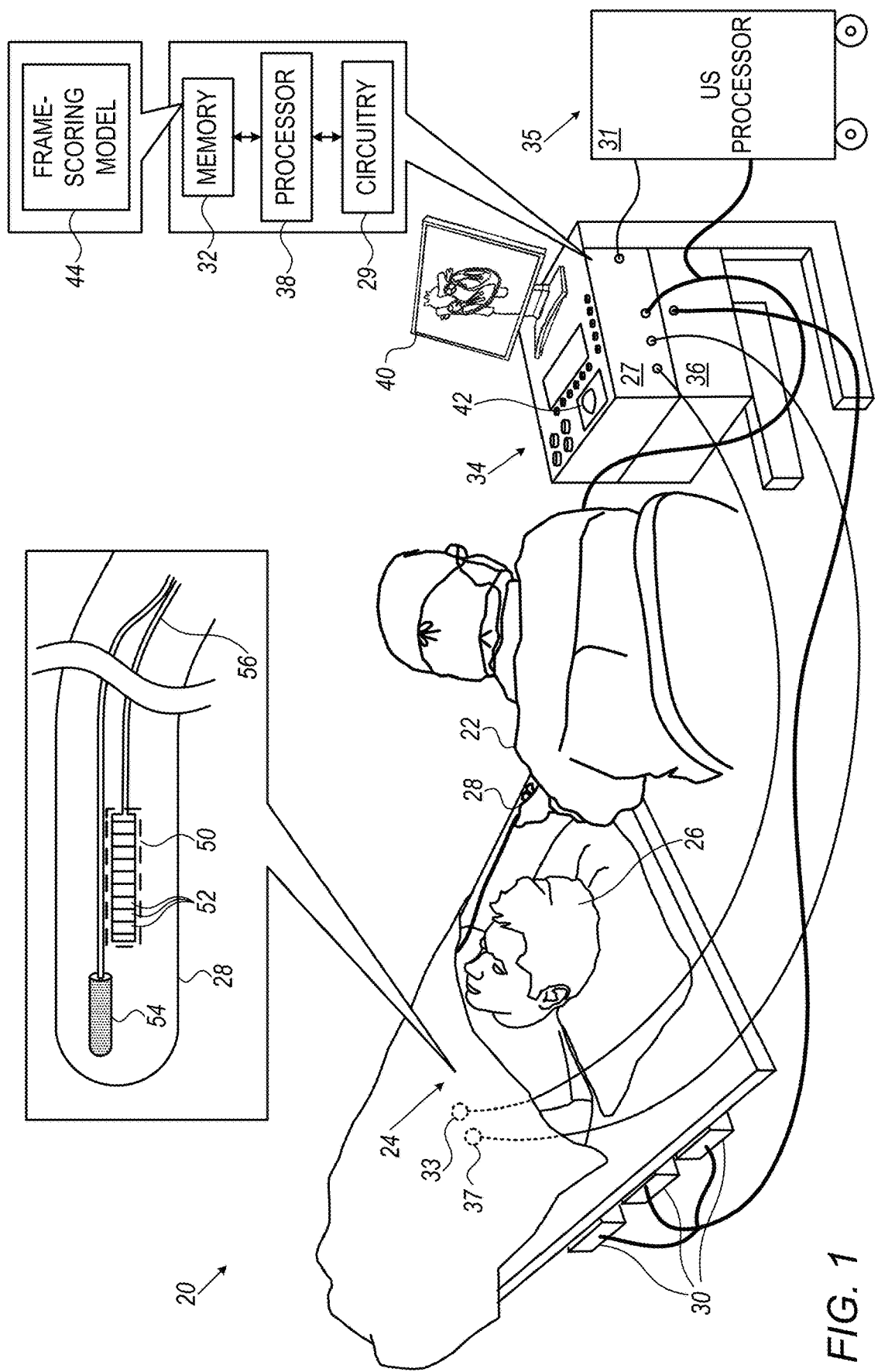
FIG. 1 is a schematic illustration of an ultrasound imaging and frame-selection system, in accordance with some embodiments of the present invention.

Reference is initially made to FIG. 1, which is a schematic illustration of an ultrasound imaging and frame-selection system 20, in accordance with some embodiments of the present invention.

System 20 comprises an intrabody imaging probe 28. As shown in FIG. 1, a physician 22 may navigate probe 28 through the vascular system of a subject 26 until the distal end of the probe is positioned within the heart 24 of subject 26. Subsequently, physician 22 may use the probe to image intracardiac tissue of the subject.

More specifically, the distal end of probe 28 comprises an ultrasound imaging device 50 comprising one or more transducers 52. Transducers 52 are configured to emit ultrasonic waves at the subject's intracardiac tissue, receive reflections of these waves, and output signals in response to the reflections. The signals are carried by wires 56 running through probe 28 to an ultrasound processor 31, which may be disposed, for example, within a first console 35. Based on the signals, using standard techniques known in the art, ultrasound processor 31 constructs ultrasound frames showing the interior of heart 24. In this manner, system 20 may acquire, for example, 20-40 frames/s.

In some embodiments, each ultrasound frame is two-dimensional. (A 2D frame may alternatively be referred to as an "image.") In other embodiments, each ultrasound frame is three-dimensional. (A 3D frame may alternatively be referred to as a "volume.")

System 20 further comprises a mapping subsystem 27, which is typically disposed within a second console 34. Mapping subsystem 27 comprises mapping circuitry 29, a mapping processor 38, and a memory 32 comprising a volatile memory, such as a random access memory (RAM), and/or a non-volatile memory. Memory 32 is configured to store a frame-scoring model 44, which typically comprises a neural network.

Mapping processor 38 is configured to receive a stream of acquired ultrasound frames from ultrasound processor 31 over any suitable wired or wireless interface. As the stream is received, the mapping processor separates the frames into sets of consecutive frames, referred to herein as "clips." Each clip may include any suitable number of frames, such as between 60 and 120 frames.

The distal end of probe 28 further comprises a tracking sensor 54, which outputs tracking signals indicating the location and orientation of the sensor within the body. The tracking signals are carried by wires 56 to mapping circuitry 29, which comprises an analog-to-digital (A/D) converter and, optionally, a noise filter and/or other signal-processing circuits. After digitizing and, optionally, otherwise processing the tracking signals, mapping circuitry 29 passes the tracking signals to mapping processor 38. Based on the tracking signals, the mapping processor ascertains the location and orientation of the 2D or 3D anatomical slice represented in each frame.

In some embodiments, tracking sensor 54 comprises an electromagnetic sensor. A driver circuit 36 in console 34 drives field generators 30 to generate a magnetic field, which induces the aforementioned tracking signals in tracking sensor 54.

In other embodiments, the tracking sensor comprises an impedance-based or ultrasonic sensor.

Typically, system 20 further comprises multiple electrocardiographic (ECG) electrodes 33, which are coupled to the subject's body. (For ease of illustration, only one electrode 33 is shown.) Signals from electrodes 33, which track the cardiac cycle of the subject, are received by mapping circuitry 29. After digitizing and, optionally, otherwise processing the ECG signals, the mapping circuitry passes the ECG signals to mapping processor 38. Based on the ECG signals, the mapping processor ascertains the phase of the subject's cardiac cycle during which each frame is acquired.

Typically, the mapping processor further ascertains the phase of the subject's respiratory cycle during which each frame is acquired.

For example, in some embodiments, system 20 further comprises multiple electrode patches 37, which are coupled to the subject's body. (For ease of illustration, only one electrode patch 37 is shown.) Electric currents are passed between the electrode patches, and the resulting signals at the electrode patches are received by mapping circuitry 29. (As the subject breathes, the impedance of the subject's body changes, such that the signals at electrode patches 37 vary over the respiratory cycle. Hence, the signals from patches 37 track the respiratory cycle of the subject.) After digitizing and, optionally, otherwise processing these signals, the mapping circuitry passes these signals to mapping processor 38. Based on these signals (and, optionally, on the position of the probe), the mapping processor ascertains the respiratory phase at which each frame was acquired.

Alternatively or additionally, the mapping processor may ascertain the respiratory phase based on a signal received from a location sensor on the subject's chest.

Typically, system 20 further comprises a display 40 configured to display any acquired ultrasound frames, along with any outputs from the mapping processor, such as the warnings described below with reference to FIGS. 2-3. In some embodiments, display 40 further shows the location and orientation of the distal end of the probe, e.g., by superimposing an icon representing the distal end of the probe over an image (or a simulated image) of the heart.

Typically, system 20 further comprises one or more input devices 42, using which physician 22 may provide system 20 with any suitable inputs. The inputs may be transferred between the first and second consoles over any suitable wired or wireless interface.

In other embodiments, probe 28 comprises an external ultrasound imaging device, which may be placed against the chest of subject 26 so as to acquire ultrasonic frames as described above.

In general, mapping processor 38 may be embodied as a single processor, or as a cooperatively networked or clustered set of processors. The functionality of mapping processor 38 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, mapping processor 38 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the mapping processor in electronic form, over a network, for example. Alternatively or additionally, the program code and/or data may be provided and/or stored on non-transitory tangible media, such as magnetic, optical, or electronic memory. Such program code and/or data, when provided to the mapping processor, produce a machine or special-purpose computer, configured to perform the tasks described herein.

In some embodiments, the functionality of the mapping processor is split over several modules, each of which may be implemented in hardware, software, or a combination of hardware and software elements. In this regard, reference is additionally made to FIG. 2, which is an example module diagram for mapping processor 38, in accordance with some embodiments of the present invention.

In some embodiments, the mapping processor executes an ultrasound-frame (US-frame) receiver 76, configured to receive a stream of ultrasound frames from ultrasound processor 31 and to separate the frames into clips, as described above.

The mapping processor further executes an ECG-signal receiver 78, configured to receive the processed ECG signals from circuitry 29. The mapping processor further executes a patch-signal receiver 80, configured to receive the processed patch signals, which track the respiratory cycle of the subject, from circuitry 29. The mapping processor further executes a tracking-signal receiver 82, configured to receive the processed tracking signals, which track the location and orientation of sensor 54, from circuitry 29.

Each of the four aforementioned modules passes its received data to a frame/metadata associator 84. By correlating between the signals and the respective times at which the frames were acquired, frame/metadata associator 84 ascertains metadata for each frame, and associates the metadata with the frame. The metadata typically include the cardiac phase and respiratory phase at which the frame was acquired, along with the location and orientation of the slice represented in the frame.

Each clip of ultrasound frames, together with its associated metadata, is passed to a frame filterer 86, which filters the clip based on the respective cardiac and/or respiratory phases at which the frames in the clip were acquired. Those frames that pass through the filter(s) are passed to a frame scorer 88, which scores the frames for image quality. Based on the scores, a frame selector 90 may select some of the frames for subsequent use. The selected frames may then be stored in memory 32 by a frame storer 92. Alternatively or additionally, if an insufficient number of frames were selected, a warning outputter 94 may output a warning. Further details regarding the functionality of frame filterer 86, frame scorer 88, frame selector 90, and warning outputter 94 are provided below with reference to FIG. 3.

Figure 2:
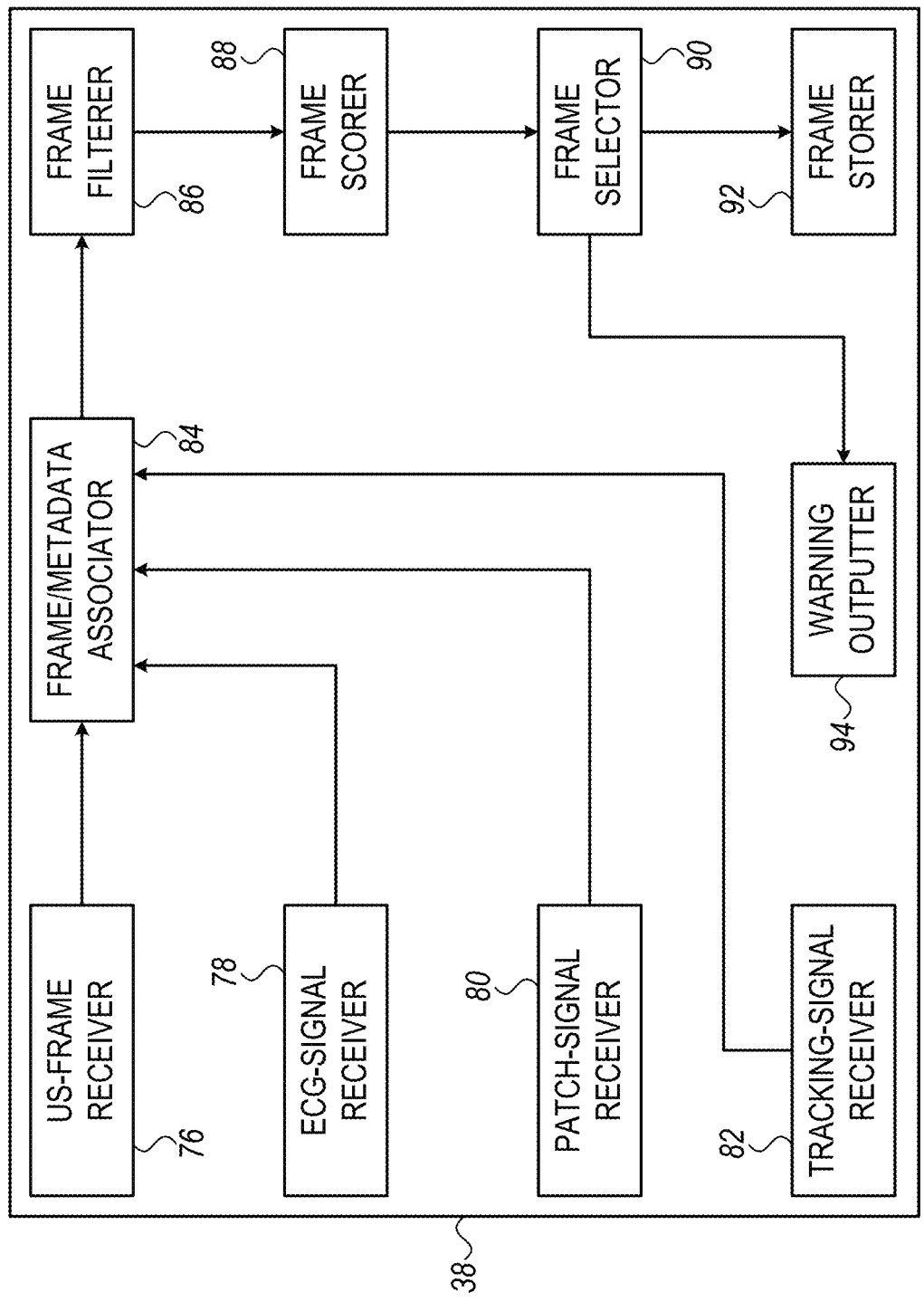
FIG. 2 is an example module diagram for a mapping processor, in accordance with some embodiments of the present invention.

It is emphasized that the module diagram in FIG. 2 is provided by way of example only, and that the functionality of the mapping processor may be split over any suitable set of modules.

Filtering, Scoring, and Selecting Frames

Figure 3:
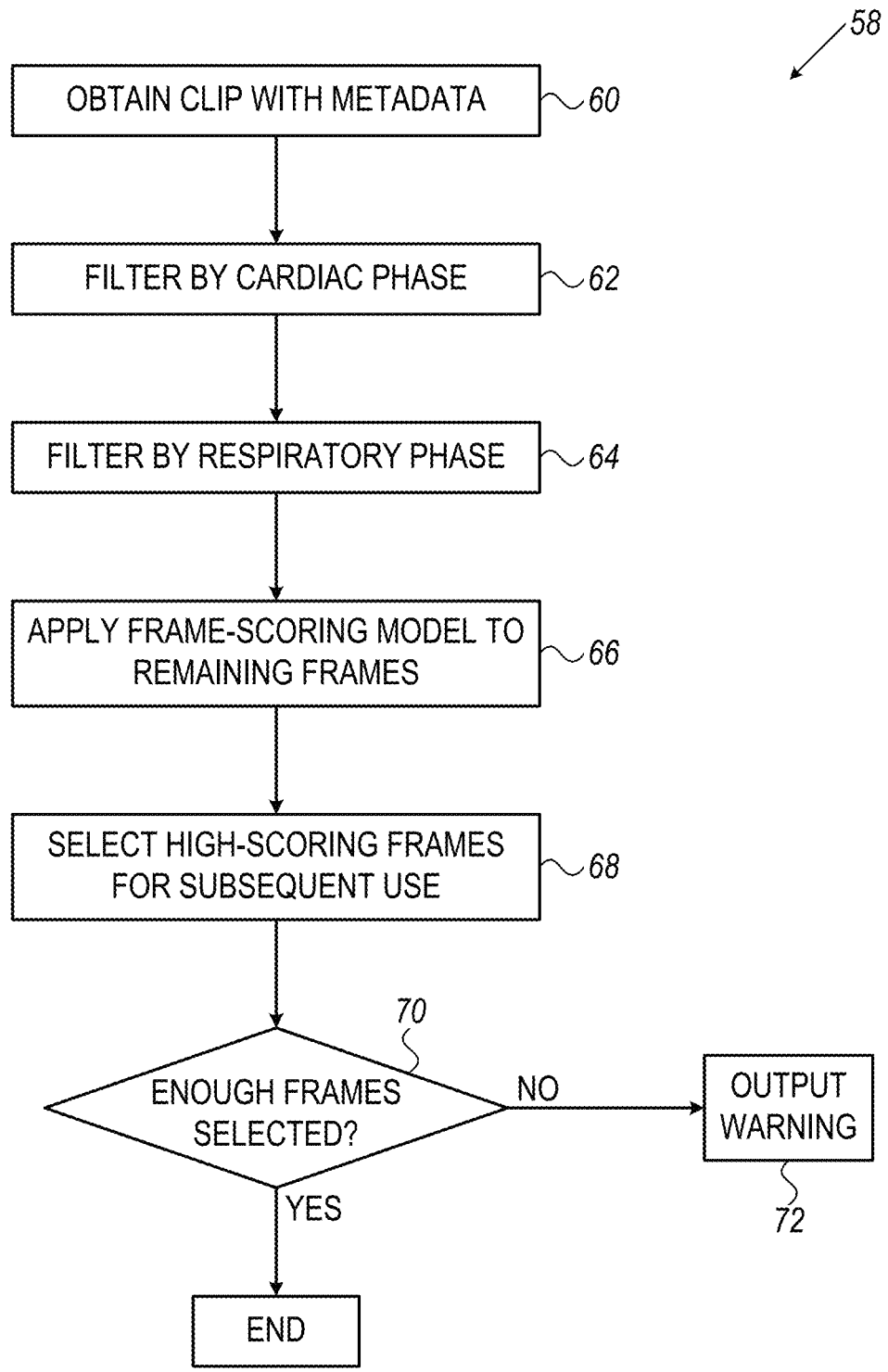
FIG. 3 is a flow diagram for an algorithm for selecting ultrasound frames showing one or more anatomical portions of interest, in accordance with some embodiments of the present invention.

Reference is now made to FIG. 3, which is a flow diagram for an algorithm 58 for selecting ultrasound frames showing one or more anatomical portions of interest, in accordance with some embodiments of the present invention. Algorithm 58, or any suitable substitute algorithm performing functions similar to those of algorithm 58, is executed by mapping processor 38 (FIG. 1).

Algorithm 58 begins at a clip-obtaining step 60, at which the mapping processor obtains a clip of ultrasound frames acquired from subject 26 (FIG. 1), along with associated metadata. For example, as described above with reference to FIG. 2, frame filterer 86 may receive the clip and metadata from frame/metadata associator 84. Alternatively, the mapping processor may read the clip and metadata from a local or remote storage device, such as a hard drive or flash drive.

As described above with reference to FIG. 2, the metadata typically include the respective cardiac and respiratory phases at which the frames belonging to the clip were acquired. Alternatively, the metadata may include only the cardiac phases, or only the respiratory phases. In any case, based on the portion of the metadata relating to the physiological cycle(s) of the subject, the mapping processor identifies a subset of the frames responsively to the subset having been acquired at one or more predefined phases of the physiological cycle(s).

For example, per algorithm 58, subsequently to obtaining the clip and metadata, the mapping processor performs a first filtering step 62, at which the mapping processor filters the clip by cardiac phase, followed by a second filtering step 64, at which the mapping processor filters the clip by respiratory phase. Alternatively, second filtering step 64 may be performed prior to first filtering step 62. As described above with reference to FIG. 2, these filtering steps may be performed by frame filterer 86.

More specifically, at first filtering step 62, the mapping processor retains those frames acquired at one or more predefined phases of the cardiac cycle, while discarding those frames acquired at different phases. A predefined phase may correspond to any suitable portion of the subject's ECG signal, such as an interval spanning the end of the T-wave. Typically, first filtering step 62 retains 1-5 frames from each cardiac cycle, the number of frames varying as a function of the length of the predefined phase and the rate at which the frames were acquired. Thus, for example, assuming the clip includes 90 frames acquired over approximately three seconds and spanning 3-4 cardiac cycles, first filtering step 62 may retain 5-20 frames while filtering out the remaining frames.

Similarly, at second filtering step 64, the mapping processor retains those frames acquired at one or more predefined phases of the respiratory cycle, such as the end-expiration phase, while discarding those frames acquired at different phases. Typically, second filtering step 64 retains around 50% of the frames from each respiratory cycle. Thus, for example, assuming the first filtering step retains 5-20 frames and the second filtering step is performed subsequently to the first filtering step, the second filtering step may retain 2-10 frames while discarding the remainder.

Subsequently to filtering the clip, the mapping processor, at a scoring step 66, applies frame-scoring model 44 (FIG. 1) to the remaining frames so as to compute respective image-quality scores for these frames. Each of the scores quantifies the image quality with which one or more anatomical portions of interest are shown in a respective one of the frames. Typically, as assumed below, a higher score indicates higher image quality, though the opposite convention may alternatively be used. As described above with reference to FIG. 2, scoring step 66 may be performed by frame scorer 88.

For example, the mapping processor may compute a respective score for each anatomical portion of interest shown in the frame, such that multiple scores may be computed for a single frame. Alternatively, the mapping processor may compute a single score for each frame.

Subsequently, based on the image-quality scores, the mapping processor, at a frame-selecting step 68, selects any high-scoring frames for subsequent use. As described above with reference to FIG. 2, frame-selecting step 68 may be performed by frame selector 90.

For example, for embodiments in which a single score is computed per frame, the mapping processor may select each frame whose score exceeds a predefined image-quality-score threshold. Optionally, the number of selected frames may be capped, i.e., the mapping processor may select no more than N frames (even if more than N scores exceed the image-quality-score threshold), N being any predetermined positive integer. For embodiments in which the scores are computed per anatomical portion, the mapping processor may select each frame having at least one score exceeding a predefined image-quality-score threshold. (Optionally, the anatomical portions may have different respective image-quality-score thresholds.)

In some embodiments, the anatomical portions of interest include one or more of the following: a left atrium body, a pulmonary vein (PV), a left atrial appendage, a left ventricle (LV) endocardium, an LV epicardium, a posteromedial papillary muscle, an anterolateral papillary muscle, a left coronary cusp, a right coronary cusp, a non-coronary cusp, and a coronary sinus.

Following frame-selecting step 68, the mapping processor checks, at a checking step 70, whether enough frames were selected. In particular, for embodiments in which a single score is computed per frame, the mapping processor compares the number of selected frames to the frame-number threshold. For embodiments in which the scores are computed per anatomical portion, the mapping processor, for each of the anatomical portions, counts the number of selected frames in which the score for the anatomical portion exceeds the image-quality-score threshold, and then compares this count with the frame-number threshold. (Optionally, the anatomical portions may have different respective frame-number thresholds.) Checking step 70 may be performed by frame selector 90 or by warning outputter 94 (FIG. 2).

If enough frames were selected, algorithm 58 ends. Otherwise, the mapping processor outputs a warning (typically by displaying the warning) at a warning step 72. In response to the warning, the physician may acquire another clip. As described above with reference to FIG. 2, warning step 72 may be performed by warning outputter 94.

In alternate embodiments, scoring step 66 is performed prior to first filtering step 62 and/or second filtering step 64. For example, the entire clip may be scored prior to any filtering of the clip.

In some embodiments, each selected frame is used for building a three-dimensional anatomical model. For example, features of the anatomical portions of interest shown in the frame may be incorporated into the model, or the anatomical portions may be tagged in the model. (In such embodiments, 1-3 frames showing each anatomical portion of interest with sufficient image quality may be required, i.e., the aforementioned frame-number threshold may be between 1 and 3.) Alternatively or additionally, a selected frame may be used to track anatomical changes over time.

The Frame-Scoring Model

In some embodiments, the frame-scoring model includes a machine-learned model.

For example, in some embodiments, the frame-scoring model includes a neural network, such as a convolutional neural network (CNN). Such a neural network may be derived from any suitable conventional neural network used in computer-vision applications. An example of such a conventional neural network is an edition of the Inception Convolutional Neural Network (e.g., Inception-v3 or Inception-ResNet-v2), which is described in Szegedy, Christian, et al., "Going deeper with convolutions," Proceedings of the IEEE conference on computer vision and pattern recognition, 2015, whose disclosure is incorporated herein by reference. Another example is an edition of the Residual Neural Network (e.g., ResNet50), which is described in He, Kaiming, et al., "Deep residual learning for image recognition," Proceedings of the IEEE conference on computer vision and pattern recognition, 2016, whose disclosure is incorporated herein by reference. Yet another example is an edition of the Visual Geometry Group neural network (e.g., VGG-19), which is described in Simonyan, Karen, and Andrew Zisserman, "Very deep convolutional networks for large-scale image recognition," arXiv preprint arXiv: 1409.1556 (2014), whose disclosure is incorporated herein by reference.

For example, the last few (e.g., the last two) layers of a conventional neural network may be replaced with two dense layers including a single output neuron configured to output an image-quality score. A similar modification to Inception-v3 and Inception-ResNet-v2 is described, for example, in Kaur, Taranjit, and Tapan Kumar Gandhi, "Deep convolutional neural networks with transfer learning for automated brain image classification," Machine Vision and Applications 31.3 (2020): 1-16, whose disclosure is incorporated herein by reference. Another similar modification to Inception-v3 and ResNet50 is described, for example, in Vesal, Sulaiman, et al., "Classification of breast cancer histology images using transfer learning," International conference image analysis and recognition, Springer, Cham, 2018, whose disclosure is incorporated herein by reference.

The neural network is trained on a learning set including a large number of ultrasound frames. In some embodiments, each frame in the learning set (or each anatomical portion of interest shown in the frame) is tagged as "high image-quality" or "low image-quality," and the image-quality score is the probability that the scored frame (or anatomical portion) belongs to the "high image-quality" class.

In some such embodiments, the frame-scoring model further includes an auxiliary neural network, which is trained to ascertain which anatomical portions of interest are shown in any given frame.

The output from the auxiliary neural network is passed as input to the frame-scoring neural network. Alternatively, the anatomical portions of interest may be identified implicitly by the frame-scoring neural network during the scoring process.

Typically, for each frame, the slice location and orientation, which are included in the aforementioned metadata, are input to the frame-scoring neural network or to the auxiliary neural network.

In other embodiments, the mapping processor computes the image-quality scores without inputting the frames to a machine-learned model. For example, given that the quality of a frame is a function of the sharpness of the blood-tissue boundaries shown in the frame, the mapping processor may score each frame based on the magnitudes of the gradients between the pixels or voxels in the frame. Alternatively or additionally, the mapping processor may score each frame based on the degree to which the frame matches one or more predefined patterns representing the relevant anatomical portions of interest.

Figure 4:
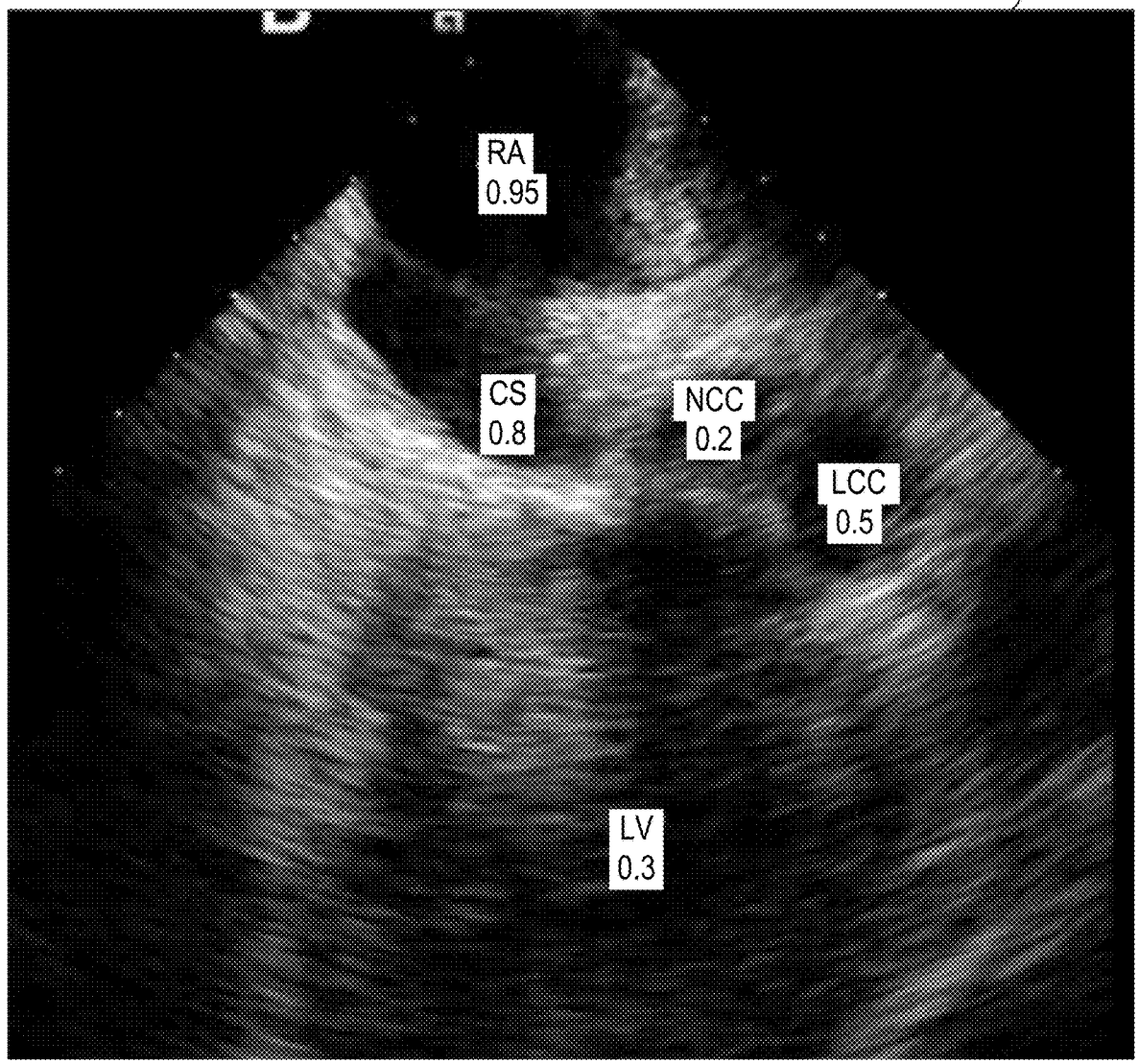
FIG. 4 is a schematic illustration of an ultrasound frame scored in accordance with some embodiments of the present invention.

Reference is now made to FIG. 4, which is a schematic illustration of an ultrasound frame 74 scored in accordance with some embodiments of the present invention.

Frame 74 shows a right atrium (RA), a coronary sinus (CS), a non-coronary cusp (NCC), a left coronary cusp (LCC), and a left ventricle (LV). In this example, the score is on a scale of 0-1, with 1 corresponding to the highest image quality. The RA and CS, whose blood-tissue boundaries are relatively sharp, have relatively high scores, while the other anatomical portions have lower scores.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
circuitry, configured to receive and process a first signal tracking a first physiological cycle of a subject and a second signal tracking a second physiological cycle of the subject; and
a processor, configured to:
receive the first signal and the second signal from the circuitry following the processing of the first signal and the second signal,
obtain a set of ultrasound frames showing a portion of a heart of the subject,
based on the first signal and the second signal, identify a subset of the frames responsively to the subset having been acquired at one or more predefined phases of the first physiological cycle and the second physiological cycle,
compute respective image-quality scores for at least the subset of the frames, each of the scores quantifying an image quality with which one or more anatomical portions of interest are shown in a respective one of the frames, and
based on the image-quality scores, select, for subsequent use, at least one frame from the subset of the frames.

2. The system according to claim 1, wherein one of the first physiological cycle and the second physiological cycle includes a respiratory cycle.

3. The system according to claim 1, wherein one of the first physiological cycle and the second physiological cycle includes a cardiac cycle.

4. The system according to claim 1, wherein the processor is configured to select the frame for use in building a three-dimensional anatomical model.

5. The system according to claim 1, wherein the anatomical portions of interest include an anatomical portion selected from the group of anatomical portions consisting of: a left atrium body, a pulmonary vein (PV), a left atrial appendage, a left ventricle (LV) endocardium, an LV epicardium, a posteromedial papillary muscle, an anterolateral papillary muscle, a left coronary cusp, a right coronary cusp, a non-coronary cusp, and a coronary sinus.

6. The system according to claim 1, wherein the processor is configured to compute the image-quality scores using a neural network.

7. The system according to claim 1, wherein the set includes between 60 and 120 frames.

8. The system according to claim 1, wherein the processor is further configured to:
ascertain that a number of the image-quality scores passing a predefined image-quality-score threshold is less than a predefined frame-number threshold, and in response to the ascertaining, output a warning.

9. A method, comprising:
obtaining, by a processor, a set of ultrasound frames showing a portion of a heart of a subject;
identifying a subset of the frames, responsively to the subset having been acquired at one or more predefined phases of a first physiological cycle of the subject and a second physiological cycle of the subject;
computing respective image-quality scores for at least the subset of the frames, each of the scores quantifying an image quality with which one or more anatomical portions of interest are shown in a respective one of the frames; and based on the image-quality scores, selecting, for subsequent use, at least one frame from the subset of the frames.

10. The method according to claim 9, wherein one of the first physiological cycle and the second physiological cycle includes a respiratory cycle.

11. The method according to claim 9, wherein one of the first physiological cycle and the second physiological cycle includes a cardiac cycle.

12. The method according to claim 9, wherein selecting the frame comprises selecting the frame for use in building a three-dimensional anatomical model.

13. The method according to claim 9, wherein the anatomical portions of interest include an anatomical portion selected from the group of anatomical portions consisting of: a left atrium body, a pulmonary vein (PV), a left atrial appendage, a left ventricle (LV) endocardium, an LV epicardium, a posteromedial papillary muscle, an anterolateral papillary muscle, a left coronary cusp, a right coronary cusp, a non-coronary cusp, and a coronary sinus.

14. The method according to claim 9, wherein computing the image-quality scores comprises computing the image-quality scores using a neural network.

15. The method according to claim 9, wherein the set includes between 60 and 120 frames.

16. The method according to claim 9, further comprising:
ascertaining that a number of the image-quality scores passing a predefined image-quality-score threshold is less than a predefined frame-number threshold; and
in response to the ascertaining, outputting a warning.

17. A computer software product comprising a tangible non-transitory computer-readable medium in which program instructions are stored, which instructions, when read by a processor, cause the processor to:
obtain a set of ultrasound frames showing a portion of a heart of a subject,
identify a subset of the frames,
responsively to the subset having been acquired at one or more predefined phases of a first physiological cycle of the subject and a second physiological cycle of the subject, compute respective image-quality scores for at least the subset of the frames, each of the scores quantifying an image quality with which one or more anatomical portions of interest are shown in a respective one of the frames, and
based on the image-quality scores, select, for subsequent use, at least one frame from the subset of the frames.

18. The computer software product according to claim 17, wherein one of the first physiological cycle and the second physiological cycle includes a respiratory cycle.

19. The computer software product according to claim 17, wherein one of the first physiological cycle and the second physiological cycle includes a cardiac cycle.

20. The computer software product according to claim 17, wherein the instructions cause the processor to compute the image-quality scores using a neural network.

* * * * *